United States Patent
Jia et al.

(10) Patent No.: US 9,125,720 B2
(45) Date of Patent: Sep. 8, 2015

(54) CAPSULARHEXIS DEVICE WITH FLEXIBLE HEATING ELEMENT

(75) Inventors: Guangyao Jia, Irvine, CA (US); Glenn Sussman, Laguna Nigel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 428 days.

(21) Appl. No.: 12/249,982

(22) Filed: Oct. 13, 2008

(65) Prior Publication Data

US 2010/0094278 A1    Apr. 15, 2010

(51) Int. Cl.
| | |
|---|---|
| *A61B 18/18* | (2006.01) |
| *A61B 18/04* | (2006.01) |
| *A61F 9/007* | (2006.01) |
| *A61B 18/10* | (2006.01) |
| *A61B 18/00* | (2006.01) |

(52) U.S. Cl.
CPC ............. *A61F 9/00754* (2013.01); *A61B 18/10* (2013.01); *A61B 2018/00642* (2013.01)

(58) Field of Classification Search
CPC ................ A61F 9/00754; A61B 18/10; A61B 2018/00642
USPC .................................................. 606/28, 29, 41
See application file for complete search history.

(56) References Cited

U.S. PATENT DOCUMENTS

| | | |
|---|---|---|
| 547,867 A | 10/1895 | Taft |
| 560,167 A | 5/1896 | Holmes |
| 974,879 A | 11/1910 | Gwinn |
| 3,159,161 A | 12/1964 | Ness |
| 3,539,034 A | 11/1970 | Woo |
| 3,809,093 A | 5/1974 | Abraham |
| 3,844,272 A | 10/1974 | Banko |
| 3,915,172 A | 10/1975 | Wichterle et al. |
| 3,949,750 A | 4/1976 | Freeman |
| 4,002,169 A | 1/1977 | Cupler, II |
| 4,026,295 A | 5/1977 | Lieberman |
| 4,068,664 A | 1/1978 | Sharp et al. |

(Continued)

FOREIGN PATENT DOCUMENTS

| | | |
|---|---|---|
| CN | 2501478 Y | 7/2002 |
| DE | 3038024 A1 | 4/1982 |

(Continued)

OTHER PUBLICATIONS

Bretton, Randolph H. et al., "Use of bipolar diathermy to prevent posterior capsule opacification," Journal of Cataract Refractive Surgery 2002; 2 8:866-878.

(Continued)

*Primary Examiner* — Theodore Stigell (57) ABSTRACT

A capsularhexis device comprises a resistive-heating element formed from an electrically resistive, superelastic wire formed into a loop. A bare surface of this loop is applied to the anterior capsule and electrically heated to define a rhexis boundary, such that a smooth circular or oval capsule portion may be removed. In some embodiments, the superelastic wire is formed to include a loop, so that first and second ends of the wire are adjacent to one another and extend away from the loop to form a lead section. An electrically insulating material may completely or partly surround the first and second ends of the wire so that the first and second ends of the superelastic wire are electrically separated. A handle engages at least a portion of the lead section so that the loop-shaped heating element may be moved in and out of the anterior chamber.

10 Claims, 4 Drawing Sheets

(56) References Cited

U.S. PATENT DOCUMENTS

| | | | |
|---|---|---|---|
| 4,210,146 A | 7/1980 | Banko | |
| 4,301,802 A | 11/1981 | Poler | |
| 4,315,509 A | 2/1982 | Smit | |
| 4,367,744 A | 1/1983 | Sole | |
| 4,368,734 A | 1/1983 | Banko | |
| 4,425,908 A | 1/1984 | Simon | |
| 4,457,757 A | 7/1984 | Molteno | |
| 4,481,948 A | 11/1984 | Sole | |
| 4,485,816 A | 12/1984 | Krumme | |
| 4,501,274 A | 2/1985 | Skjaerpe | |
| 4,530,356 A | 7/1985 | Helfgott et al. | |
| 4,530,359 A | 7/1985 | Helfgott et al. | |
| 4,531,934 A | 7/1985 | Kossovsky et al. | |
| 4,559,942 A | 12/1985 | Eisenberg | |
| 4,570,632 A | 2/1986 | Woods | |
| 4,607,622 A | 8/1986 | Fritch et al. | |
| 4,616,656 A | 10/1986 | Nicholson et al. | |
| 4,665,906 A | 5/1987 | Jervis | |
| 4,676,243 A | 6/1987 | Clayman | |
| 4,706,669 A | 11/1987 | Schlegel | |
| 4,706,671 A | 11/1987 | Weinrib | |
| 4,708,138 A | 11/1987 | Pazandak | |
| 4,729,761 A | 3/1988 | White | |
| 4,766,896 A | 8/1988 | Pao | |
| 4,766,897 A | 8/1988 | Smirmaul | |
| 4,781,675 A | 11/1988 | White | |
| 4,805,616 A | 2/1989 | Pao | |
| 4,869,248 A | 9/1989 | Narula | |
| 4,869,716 A | 9/1989 | Smirmaul | |
| 4,885,004 A | 12/1989 | Pao | |
| 4,900,300 A | 2/1990 | Lee | |
| 4,911,161 A | 3/1990 | Schechter | |
| 4,936,825 A | 6/1990 | Ungerleider | |
| 4,950,272 A | 8/1990 | Smirmaul | |
| 4,955,859 A | 9/1990 | Zilber | |
| 4,955,894 A | 9/1990 | Herman | |
| 4,986,825 A | 1/1991 | Bays et al. | |
| 4,994,066 A | 2/1991 | Voss | |
| 5,047,008 A | 9/1991 | de Juan, Jr. et al. | |
| 5,085,664 A | 2/1992 | Bozzo | |
| 5,123,906 A | 6/1992 | Kelman | |
| 5,135,530 A | 8/1992 | Lehmer | |
| 5,180,362 A | 1/1993 | Worst | |
| 5,188,634 A | 2/1993 | Hussein et al. | |
| 5,199,445 A | 4/1993 | Rubinfeld | |
| 5,203,865 A | 4/1993 | Siepser | |
| 5,234,436 A | 8/1993 | Eaton et al. | |
| 5,242,404 A | 9/1993 | Conley et al. | |
| 5,242,449 A | 9/1993 | Zaleski | |
| 5,261,923 A | 11/1993 | Soares | |
| 5,269,787 A | 12/1993 | Cozean, Jr. et al. | |
| 5,322,504 A | 6/1994 | Doherty et al. | |
| 5,342,377 A | 8/1994 | Laszerson | |
| 5,346,491 A | 9/1994 | Oertli | |
| 5,360,399 A | 11/1994 | Stegmann | |
| 5,364,405 A | 11/1994 | Zaleski | |
| 5,366,443 A | 11/1994 | Eggers et al. | |
| 5,374,244 A | 12/1994 | Clement et al. | |
| 5,395,361 A | 3/1995 | Fox et al. | |
| 5,411,510 A | 5/1995 | Fugo | |
| 5,413,574 A | 5/1995 | Fugo | |
| 5,423,330 A | 6/1995 | Lee | |
| 5,423,841 A | 6/1995 | Kornefeld | |
| 5,439,474 A | 8/1995 | Li | |
| 5,445,636 A | 8/1995 | Bretton | |
| 5,445,637 A * | 8/1995 | Bretton | 606/41 |
| 5,466,234 A | 11/1995 | Loeb et al. | |
| 5,478,338 A | 12/1995 | Reynard | |
| 5,484,433 A | 1/1996 | Taylor et al. | |
| 5,486,165 A | 1/1996 | Stegmann | |
| 5,486,183 A | 1/1996 | Middleman et al. | |
| 5,487,725 A | 1/1996 | Peyman | |
| 5,509,923 A | 4/1996 | Middleman et al. | |
| 5,522,829 A | 6/1996 | Michalos | |
| 5,527,332 A | 6/1996 | Clement | |
| 5,562,692 A | 10/1996 | Bair | |
| 5,569,197 A | 10/1996 | Helmus et al. | |
| 5,569,280 A | 10/1996 | Kamerling | |
| 5,601,094 A | 2/1997 | Reiss | |
| 5,601,572 A | 2/1997 | Middleman et al. | |
| 5,601,593 A | 2/1997 | Freitag | |
| 5,626,558 A | 5/1997 | Suson | |
| 5,630,827 A | 5/1997 | Vijfvinkel | |
| 5,632,746 A | 5/1997 | Middleman et al. | |
| 5,651,783 A | 7/1997 | Reynard | |
| 5,662,670 A | 9/1997 | Michalos | |
| 5,669,923 A | 9/1997 | Gordon | |
| 5,670,161 A | 9/1997 | Healy et al. | |
| 5,683,592 A | 11/1997 | Bartholomew et al. | |
| 5,700,243 A | 12/1997 | Narciso, Jr. | |
| 5,716,363 A | 2/1998 | Josephberg | |
| 5,720,754 A | 2/1998 | Middleman et al. | |
| 5,728,117 A | 3/1998 | Lash | |
| 5,733,276 A | 3/1998 | Belkin | |
| 5,733,297 A | 3/1998 | Wang | |
| 5,741,244 A | 4/1998 | Klaas | |
| 5,749,879 A | 5/1998 | Middleman et al. | |
| 5,755,731 A | 5/1998 | Grinberg | |
| 5,766,171 A | 6/1998 | Silvestrini | |
| 5,792,166 A | 8/1998 | Gordon et al. | |
| 5,820,628 A | 10/1998 | Middleman et al. | |
| 5,827,321 A | 10/1998 | Roubin et al. | |
| 5,843,019 A | 12/1998 | Eggers et al. | |
| 5,860,994 A | 1/1999 | Yaacobi | |
| 5,865,800 A * | 2/1999 | Mirarchi et al. | 604/95.04 |
| 5,868,697 A | 2/1999 | Richter et al. | |
| 5,873,883 A | 2/1999 | Cozean, Jr. et al. | |
| 5,885,279 A * | 3/1999 | Bretton | 606/41 |
| 5,888,201 A | 3/1999 | Stinson et al. | |
| 5,891,084 A | 4/1999 | Lee | |
| 5,893,862 A | 4/1999 | Pratt et al. | |
| 5,898,697 A | 4/1999 | Hurme et al. | |
| 5,904,690 A | 5/1999 | Middleman et al. | |
| 5,911,729 A | 6/1999 | Shikhman et al. | |
| 5,921,999 A | 7/1999 | Dileo | |
| 5,925,056 A | 7/1999 | Thomas et al. | |
| 5,957,921 A | 9/1999 | Mirhashemi et al. | |
| 5,989,262 A | 11/1999 | Josephberg | |
| 6,004,330 A | 12/1999 | Middleman et al. | |
| 6,036,688 A * | 3/2000 | Edwards | 606/34 |
| 6,059,792 A | 5/2000 | Josephberg | |
| 6,066,138 A * | 5/2000 | Sheffer et al. | 606/49 |
| 6,135,998 A | 10/2000 | Palanker | |
| 6,142,996 A | 11/2000 | Mirhashemi et al. | |
| 6,162,202 A | 12/2000 | Sicurelli et al. | |
| 6,165,190 A | 12/2000 | Nguyen | |
| D436,663 S | 1/2001 | Chandler et al. | |
| D437,054 S | 1/2001 | Chandler et al. | |
| 6,179,830 B1 | 1/2001 | Kokubu | |
| D437,413 S | 2/2001 | Chandler et al. | |
| 6,203,518 B1 | 3/2001 | Anis et al. | |
| 6,217,598 B1 | 4/2001 | Berman et al. | |
| 6,241,721 B1 | 6/2001 | Cozean et al. | |
| 6,264,668 B1 | 7/2001 | Prywes | |
| 6,306,155 B1 | 10/2001 | Chandler et al. | |
| 6,379,370 B1 | 4/2002 | Feinsod | |
| 6,413,262 B2 | 7/2002 | Saishin et al. | |
| 6,440,103 B1 | 8/2002 | Hood et al. | |
| 6,447,523 B1 | 9/2002 | Middleman et al. | |
| 6,503,263 B2 | 1/2003 | Adams | |
| 6,506,176 B1 | 1/2003 | Mittelstein et al. | |
| 6,527,766 B1 | 3/2003 | Bair | |
| 6,544,254 B1 | 4/2003 | Bath | |
| 6,551,326 B1 | 4/2003 | Van Heugten et al. | |
| 6,575,929 B2 | 6/2003 | Sussman et al. | |
| 6,616,996 B1 | 9/2003 | Keith et al. | |
| 6,629,980 B1 | 10/2003 | Eibschitz-Tsimhoni | |
| 6,673,064 B1 | 1/2004 | Rentrop | |
| 6,764,439 B2 | 7/2004 | Schaaf et al. | |
| 6,979,328 B2 | 12/2005 | Baerveldt et al. | |
| 6,986,774 B2 | 1/2006 | Middleman et al. | |
| 7,011,666 B2 | 3/2006 | Feinsod | |
| 7,135,009 B2 | 11/2006 | Tu et al. | |
| 7,585,295 B2 | 9/2009 | Ben-Nun | |

(56) References Cited

U.S. PATENT DOCUMENTS

| | | | |
|---|---|---|---|
| 7,722,626 | B2 | 5/2010 | Middleman et al. |
| 7,785,321 | B2 | 8/2010 | Baerveldt et al. |
| 8,128,641 | B2 | 3/2012 | Wardle |
| 8,162,931 | B2 | 4/2012 | Ben-Nun |
| 8,235,978 | B2 | 8/2012 | Ben-Nun |
| 8,323,276 | B2 | 12/2012 | Palanker et al. |
| 8,512,321 | B2 | 8/2013 | Baerveldt et al. |
| 8,814,854 | B2 | 8/2014 | Jia et al. |
| 2001/0044625 | A1 | 11/2001 | Hata et al. |
| 2002/0007150 | A1 | 1/2002 | Johnson |
| 2002/0049437 | A1 | 4/2002 | Silvestrini |
| 2002/0091402 | A1 | 7/2002 | Feinsod |
| 2002/0161365 | A1 | 10/2002 | Martins |
| 2003/0009177 | A1 | 1/2003 | Sheffer et al. |
| 2004/0050392 | A1 | 3/2004 | Tu et al. |
| 2004/0092982 | A1 | 5/2004 | Sheffer |
| 2004/0106929 | A1 | 6/2004 | Masket |
| 2004/0116950 | A1 | 6/2004 | Eibschitz-Tsimhoni |
| 2004/0220564 | A1* | 11/2004 | Ho et al. ............ 606/47 |
| 2005/0054972 | A1 | 3/2005 | Adams et al. |
| 2005/0228419 | A1 | 10/2005 | El-Mansoury |
| 2006/0036270 | A1 | 2/2006 | Terao |
| 2006/0100617 | A1 | 5/2006 | Boukhny |
| 2006/0106370 | A1 | 5/2006 | Baerveldt et al. |
| 2006/0241580 | A1 | 10/2006 | Mittelstein et al. |
| 2006/0259053 | A1 | 11/2006 | El-Mansoury |
| 2007/0010812 | A1 | 1/2007 | Mittelstein et al. |
| 2007/0049957 | A1 | 3/2007 | Benitez |
| 2007/0060926 | A1 | 3/2007 | Escaf |
| 2007/0073275 | A1 | 3/2007 | Conston et al. |
| 2007/0078359 | A1 | 4/2007 | Luloh et al. |
| 2007/0191862 | A1 | 8/2007 | Ellis |
| 2007/0239156 | A1 | 10/2007 | Palanker et al. |
| 2007/0276420 | A1 | 11/2007 | Sorensen et al. |
| 2008/0114341 | A1 | 5/2008 | Thyzel |
| 2008/0147061 | A1 | 6/2008 | Goode |
| 2009/0054904 | A1 | 2/2009 | Holmen |
| 2009/0094278 | A1 | 4/2009 | Jia et al. |
| 2009/0137992 | A1 | 5/2009 | Nallakrishnan |
| 2009/0216225 | A1 | 8/2009 | Ben-Nun |
| 2009/0240149 | A1 | 9/2009 | Peyman |
| 2009/0287143 | A1 | 11/2009 | Line |
| 2009/0287233 | A1 | 11/2009 | Huculak |
| 2010/0057069 | A1 | 3/2010 | Ben-Nun |
| 2010/0145447 | A1 | 6/2010 | Jia et al. |
| 2010/0179544 | A1 | 7/2010 | Boukhny et al. |
| 2010/0274272 | A1 | 10/2010 | Medina |
| 2010/0298820 | A1 | 11/2010 | Ben-Nun |
| 2010/0312252 | A1 | 12/2010 | Jia et al. |
| 2011/0054384 | A1 | 3/2011 | Brown |
| 2011/0087256 | A1 | 4/2011 | Wiener et al. |
| 2011/0202049 | A1 | 8/2011 | Jia et al. |
| 2011/0282335 | A1 | 11/2011 | Sussman et al. |
| 2012/0158027 | A1 | 6/2012 | Moradian et al. |
| 2012/0158130 | A1 | 6/2012 | Moradian et al. |
| 2013/0066351 | A1 | 3/2013 | Giardina et al. |
| 2013/0158573 | A1 | 6/2013 | Zaidman et al. |
| 2013/0197548 | A1 | 8/2013 | Keller |
| 2013/0289545 | A1 | 10/2013 | Baerveldt et al. |

FOREIGN PATENT DOCUMENTS

| | | |
|---|---|---|
| DE | 3205959 A1 | 9/1983 |
| DE | 3248101 A1 | 6/1984 |
| DE | 3434930 A1 | 4/1986 |
| DE | 8710541 U1 | 11/1987 |
| DE | 197 40 530 A1 | 3/1990 |
| DE | 4012882 A1 | 10/1991 |
| DE | 9311879 U1 | 11/1993 |
| DE | 19719549 A1 | 11/1998 |
| DE | 19809510 A1 | 9/1999 |
| DE | 10220253 A1 | 11/2002 |
| EP | 0170650 B1 | 8/1985 |
| EP | 183385 B1 | 3/1989 |
| EP | 165657 B1 | 7/1989 |
| EP | 0335714 A2 | 10/1989 |
| EP | 358990 A1 | 3/1990 |
| EP | 0228185 B1 | 7/1990 |
| EP | 0355341 B1 | 10/1992 |
| EP | 0537116 A1 | 4/1993 |
| EP | 506618 B1 | 7/1995 |
| EP | 0730848 A2 | 9/1996 |
| EP | 0730848 A3 | 7/1997 |
| EP | 0788802 A2 | 8/1997 |
| EP | 0898947 A2 | 3/1999 |
| EP | 0898947 A3 | 9/1999 |
| EP | 0730848 B1 | 4/2000 |
| EP | 0788802 A3 | 4/2000 |
| EP | 1010410 A1 | 6/2000 |
| EP | 1027906 A2 | 8/2000 |
| EP | 0986328 A4 | 5/2001 |
| EP | 1095641 A1 | 5/2001 |
| EP | 0788802 B1 | 7/2006 |
| EP | 1809196 A4 | 3/2008 |
| EP | 1809196 B1 | 9/2010 |
| EP | 1871216 B1 | 6/2012 |
| ES | 2 103 635 | 9/1997 |
| FR | 2544979 A1 | 11/1984 |
| FR | 2588751 A1 | 4/1987 |
| FR | 2 676 355 | 11/1992 |
| FR | 2677244 A1 | 12/1992 |
| FR | 2702955 A1 | 9/1994 |
| FR | 2707872 A1 | 1/1995 |
| FR | 2830186 A1 | 4/2003 |
| FR | 2855745 A1 | 12/2004 |
| FR | 2855746 A1 | 12/2004 |
| FR | 2924924 A1 | 6/2009 |
| GB | 2247174 A | 2/1992 |
| GB | 2437252 A | 10/2007 |
| JP | 2004-523272 | 8/2004 |
| JP | 2007014510 | 1/2007 |
| JP | 2007-83049 | 4/2007 |
| JP | 2008-538306 A | 10/2008 |
| KR | 20100016724 | 2/2010 |
| KR | 20100121583 | 11/2010 |
| KR | 101039394 B1 | 6/2011 |
| KR | 101039398 B1 | 6/2011 |
| RU | 2238710 C1 | 10/2004 |
| SU | 452338 | 12/1974 |
| SU | 1301400 A1 | 4/1987 |
| SU | 1395314 A1 | 5/1988 |
| SU | 1431752 A1 | 10/1988 |
| SU | 1440496 A1 | 11/1988 |
| SU | 1766403 A1 | 10/1992 |
| SU | 1790934 A1 | 1/1993 |
| SU | 1790935 A1 | 1/1993 |
| SU | 1148613 A1 | 4/1995 |
| WO | WO 86/02257 A1 | 4/1986 |
| WO | WO 93/01755 A1 | 2/1993 |
| WO | WO 93/20765 A1 | 10/1993 |
| WO | WO 95/08310 A1 | 3/1995 |
| WO | WO 96/06570 A1 | 3/1996 |
| WO | WO 97/26835 A1 | 7/1997 |
| WO | WO 97/30669 | 8/1997 |
| WO | WO 98/49945 A1 | 11/1998 |
| WO | WO 99/60936 A1 | 12/1999 |
| WO | WO 00/48540 A1 | 8/2000 |
| WO | WO 01/56519 A1 | 8/2001 |
| WO | WO 01/60266 A1 | 8/2001 |
| WO | WO 03/022174 | 3/2003 |
| WO | WO 03/022174 A3 | 3/2003 |
| WO | WO 03/039335 A2 | 5/2003 |
| WO | WO 03/039335 A3 | 5/2003 |
| WO | WO 03/045290 A1 | 6/2003 |
| WO | WO 2004/039295 | 5/2004 |
| WO | WO 2004/071312 A1 | 8/2004 |
| WO | WO 2006/052374 A2 | 5/2006 |
| WO | WO 2006/052374 A3 | 5/2006 |
| WO | WO 2006/109255 A1 | 10/2006 |
| WO | WO 2006/109290 A2 | 10/2006 |
| WO | WO 2006/117772 A1 | 11/2006 |
| WO | WO 2007/121485 A2 | 10/2007 |
| WO | WO 2008/080149 A1 | 7/2008 |

(56) References Cited

FOREIGN PATENT DOCUMENTS

| WO | 2008/115455 | 9/2008 |
|---|---|---|
| WO | WO 2009/140414 A1 | 11/2009 |
| WO | WO 2009/153550 A1 | 12/2009 |
| WO | WO 2010/044988 A1 | 4/2010 |
| WO | WO 2010/068662 A1 | 6/2010 |
| WO | WO 2010/141179 A1 | 12/2010 |
| WO | WO 2010/141181 A1 | 12/2010 |
| WO | WO 2011/102928 A1 | 8/2011 |
| WO | 2013/22854 A1 | 2/2013 |
| WO | 2013/070423 A1 | 5/2013 |
| WO | 2013/073609 A1 | 5/2013 |

OTHER PUBLICATIONS

Sussman, Glen et al., Capsularhexis Device with Flexible Heating Element having an Angled Transitional Neck, U.S. Appl. No. 12/477,175, filed Jun. 3, 2009, 32 pages.

International Searching Authority, International Preliminary Report on Patentability, PCT/US2005/036670, May 15, 2007, 4 pages.

Huculak, John C. et al., Capsularhexis Device Using Pulsed Electric Fields, U.S. Appl. No. 12/618,805, filed Nov. 16, 2009, 14 pages.

Jia, Guangyao, et al., Capsule Polishing Device and Method for Capsule Polishing, U.S. Appl. No. 12/777,820, filed May 11, 2010, 26 pages.

Jia, Guangyao, et al., Capsulotomy Repair Device and Method for Capsulotomy Repair, U.S. Appl. No. 12/754,119, filed Apr. 5, 2010, 40 pages.

Sussman, Glenn, et al., Small Gauge Ablation Probe for Glaucoma Surgery, U.S. Appl. No. 12/707,747, filed Feb. 18, 2010, 11 pages.

Karmel, Miriam, "Glaucoma Surgies: Trabectome and Canaloplasty Take the Stage," publication, May 2009, pp. 29-30, American Academy of Ophthalmology.

Lewandowski, Julia T., "Improving Ab Interno Trabeculotomy, A combination of advanced technology and insightful design may prompt surgeons to adopt a new technique for lowering IOP," article, Jul. 2007, 4 pages, Bryn Mawr Communications.

Abstract of SU1805938; Publication date Mar. 30, 1993; Priority date Mar. 11, 1991.

Abstract of JP4834337(B2); Publication date Dec. 14, 2011.

Della, Jaymi E., Office Action Summary, U.S. Appl. No. 12/477,175, Aug. 15, 2014, 36 pages.

Giuliani, Thomas Anthony, Office Action Summary, U.S. Appl. No. 12/777,820, Sep. 25, 2014, 13 pages.

Fowler, Daniel Wayne, Office Action Summary, U.S. Appl. No. 12/707,747, Aug. 31, 2012, 34 pages.

Della, Jaymi E., Office Action Summary, U.S. Appl. No. 12/477,175, Jun. 18, 2012, 12 pages.

Giuliani, Thomas Anthony, Office Action Summary, U.S. Appl. No. 12/777,820, Jun. 6, 2013, 40 pages.

Della, Jaymi E., Office Action Summary, U.S. Appl. No. 12/477,175, Nov. 17, 2014, 20 pages.

Della, Jaymi E., Office Action Summary, U.S. Appl. No. 12/477,175, Nov. 14, 2011, 39 pages.

Della, Jaymi E., Office Action Summary, U.S. Appl. No. 12/477,175, Feb. 28, 2012, 12 pages.

International Searching Authority, International Search Report, International Application No. PCT/US2010/033893, Jul. 8, 2010, 5 pages.

International Searching Authority, Written Opinion of the International Searching Authority, International Application No. PCT/US2010/033893, Jul. 8, 2010, 8 pages.

International Searching Authority, International Preliminary Report on Patentability, International Application No. PCT/US2009/057836, Apr. 19, 2011, 7 pages.

International Searching Authority, Written Opinion of the International Searching Authority, International Application No. PCT/US2009/057836, Apr. 19, 2011, 6 pages.

International Searching Authority, International Search Report, International Application No. PCT/US2010/033949, Jul. 23, 2010, 6 pages.

International Searching Authority, Written Opinion of the International Searching Authority, International Application No. PCT/US2010/033949, Jul. 23, 2010, 9 pages.

International Searching Authority, International Search Report, International Application No. PCT/US2011/021608, Mar. 1, 2011, 6 pages.

International Searching Authority, Written Opinion of the International Searching Authority, International Application No. PCT/US2011/021608, Mar. 1, 2011, 9 pages.

Giuliani, Thomas Anthony, Office Action Summary, U.S. Appl. No. 12/777,820, Mar. 4, 2015, 15 pages.

\* cited by examiner

CAPSULARHEXIS DEVICE WITH FLEXIBLE HEATING ELEMENT

TECHNICAL FIELD

The present invention relates generally to the field of cataract surgery and more particularly to methods and apparatus for performing a capsularhexis.

BACKGROUND

An accepted treatment for the treatment of cataracts is surgical removal of the lens and replacement of the lens function by an artificial intraocular lens (IOL). In the United States, the majority of cataractous lenses are removed by a surgical technique called phacoemulsification. Prior to removing the cataractous lens, an opening, or rhexis, must be made in the anterior capsule. During phacoemulsification, there is a great deal of tension on the cut edges of the anterior capsularhexis while the lens nucleus is emulsified. Accordingly, a continuous cut or tear (rhexis), without "tags," is a critical step in a safe and effective phacoemulsification procedure.

If the capsule is opened with numerous small capsular tears, the small tags that remain can lead to radial capsular tears which may extend into the posterior capsule. Such a radial tear constitutes a complication since it destabilizes the lens for further cataract removal and safe intraocular lens placement within the lens capsule later in the operation. Further, if the posterior capsule is punctured then the vitreous may gain access to the anterior chamber of the eye. If this happens, the vitreous must be removed by an additional procedure with special instruments. The loss of vitreous is also associated with an increased rate of subsequent retinal detachment and/or infection within the eye. Importantly, these complications are potentially blinding.

Conventional equipment used for phacoemulsification includes an ultrasonically driven handpiece with an attached cutting tip. In some of these handpieces, the operative part is a centrally located, hollow resonating bar or horn directly attached to a set of piezoelectric crystals. The crystals supply ultrasonic vibration for driving both the horn and the attached cutting tip during phacoemulsification.

Prior art devices and methods used for the capsularhexis procedure require a great deal of skill on the part of the surgeon to produce a continuous curvilinear capsular opening. This is due to the extreme difficulty in controlling the path of the cutting tip of the device. For example, a typical procedure begins with a capsular incision made with a cystotome, e.g., a cutting tip as described above. This incision is then coaxed into a circular or oval shape by pushing the leading edge of the incision in the capsule, using the cystotome as a wedge rather than in a cutting fashion. Alternatively, the initial capsular incision may be torn into a circular shape by grasping the leading edge with fine caliber forceps and advancing the cut. Either of these approaches involves a very challenging maneuver and the tearing motion can sometimes lead to an undesirable tear of the capsule toward the back of the lens, even in the most experienced hands.

Moreover, even if a smooth capsular opening without tags is ultimately produced, the size and/or position of the capsular opening may present a problem. For instance, a capsular opening that is too small can impede the safe removal of the lens nucleus and cortex and prevent proper intraocular lens insertion into the lens capsule. The additional stresses necessary to accomplish the operation with a small or misplaced capsular opening put the eye at risk for zonular and capsular breakage. Either of these complications will likely increase the length and complexity of the operation and may result in vitreous loss.

A continuous, properly positioned, and circular opening is thus highly desirable because it results in: (1) a significant reduction in radial tears and tags within the anterior capsule, (2) capsule integrity necessary for proper centering of a lens prosthesis; (3) safe and effective hydrodissection; and (4) safe use of capsular procedures on patients having poorly visualized capsules and/or small pupil openings. In addition, the capsularhexis should be properly dimensioned relative to the diameter of the IOL being implanted in order to reduce the chances of a secondary cataract, also called posterior capsule opacification ("PCO") and for use with proposed accommodative IOLs designs. Therefore, there is a continuing need for an improved device for performing an anterior chamber capsularhexis.

SUMMARY

Embodiments of the present invention include a capsularhexis device comprising a resistive-heating element formed from an electrically resistive, superelastic wire formed into a loop. A bare surface of this loop may be applied to the anterior capsule and heated with an electrical current to cause localized heating, or "burning" of the capsule. This localized burned area defines a rhexis boundary, such that a smooth circular or oval capsule portion may be removed with little risk of radial tearing.

In some embodiments, the resistive-heating element of the capsularhexis devices thus comprises an electrically resistive, superelastic wire having first and second ends, wherein the superelastic wire is formed to include a loop. The first and second ends of the wire are adjacent to one another and extend away from the loop to form a lead section. An insulation portion comprising an electrically insulating material may completely or partly surround the first and second ends of the wire at or near the lead section, so that the first and second ends of the superelastic wire are electrically separated. A handle engages at least a portion of the lead section so that the loop-shaped heating element may be moved in and out of the anterior chamber of the eye for performing the capsularhexis.

In some embodiments, the capsularhexis device may also include a tubular insertion cartridge configured to fit around the handle portion. The tubular insertion cartridge in these embodiments may be dimensioned so as to contain substantially all of the collapsed loop of the heating element when the heating element is pushed into or retracted into the insertion cartridge.

In some embodiments, the superelastic wire is formed from a nickel titanium alloy exhibiting superelastic properties. In general, the loop of the resistive-heating element has a bottom face, for placing against the anterior lens capsule of an eye, and a top face, opposite the bottom face. However, in some embodiments the resistive-heating element may further include a thermally insulating layer disposed on at least the top face but absent from the bottom face. In some of these embodiments, the superelastic wire may have a rectangular cross section around all or substantially all of the loop, so that the thermally insulating layer is disposed on three sides of the superelastic wire around all or substantially all of the loop.

An exemplary method for utilizing a capsularhexis device, according to some embodiments of the invention, begins with the positioning one end of a tubular insertion cartridge in or near the anterior chamber of an eye. The tubular insertion cartridge containing a resistive-heating element comprising an electrically resistive, superelastic wire having first and second ends, the superelastic wire formed to include a loop and so that the first and second ends are adjacent and extend away from the loop to form a lead section. Using a handle that rigidly engages at least a portion of the lead section, the loop of the resistive-heating element from the tubular insertion cartridge is ejected into the anterior chamber, and positioned in contact with the anterior lens capsule of the eye. The resistive-heating element is electrically heated to burn the lens capsule along the ejected loop, after which the loop of the resistive-heating element is retracted into the tubular insertion cartridge before removal from the eye. In some embodiments, the positioning of the ejected loop in contact with the anterior lens capsule of the eye may include positioning the ejected loop in contact with the anterior lens capsule so that a portion of the lead section between the loop and the handle is bent to an operating angle approximately equal to a pre-determined angle corresponding to a desired contact force.

Of course, those skilled in the art will appreciate that the present invention is not limited to the above features, advantages, contexts or examples, and will recognize additional features and advantages upon reading the following detailed description and upon viewing the accompanying drawings.

DETAILED DESCRIPTION

Various embodiments of the present invention provide apparatus and corresponding methods of use for performing capsularhexis. In particular, the present invention relates to a surgical instrument, a so-called capsularhexis device, which may be positioned within the anterior chamber of an eye through a small incision to perform capsularhexis, or capsulotomy. This procedure facilitates phacoemulsification of a cataractous lens and insertion of an artificial intraocular lens (IOL).

United States Patent Application Publication No. 2006/010061 describes a capsularhexis device comprising a circular, flexible ring made of an elastomer or an acrylic or thermoplastic material. Embedded within each of various embodiments of this flexible ring is either a resistance-heating element or a pair of bipolar electrodes, which are energized according to known techniques to produce localized heating on the anterior capsule, so as to define a weakened boundary for an easy detachment of the portion of the capsule within the circular ring.

According to several embodiments of the present invention, the flexible ring structure may be replaced with an at least partially bare resistance-heating element made from a super-elastic wire. By combining the super-elasticity of the wire material with a relatively high electric resistivity, a collapsible, ring-shaped heating element may be constructed to perform capsulotomy by localized heating. Because the heating element is collapsible, it may be easily inserted into the eye through a small incision (e.g., 2 mm) in the cornea.

The feasibility of using a bare wire as a heating element results from the combination of the superelastic properties of the wire, which allows the wire to collapse during insertion and return to a pre-formed circular or oval shape during use, and the fact that the anterior chamber may be inflated with a fluid, prior to the capsulotomy, with a low thermal diffusivity. The viscoelastic agent used to inflate the anterior chamber has a sufficiently low thermal diffusivity so that it serves as a thermal insulator around the heating element, thus facilitating the formation of a highly concentrated thermally affected zone in the immediate vicinity of the heating element. The concentration of this zone minimizes collateral damage to nearby tissue. Although in practice it may be unavoidable to trap a thin film of viscoelastic material between the heating element and the capsule, a small defined area on the capsule will still respond sufficiently fast to the temperature rise in the heating element to avoid collateral damage, due to the small thickness (e.g., 10 micrometers) of the fluid film.

Figure 1:
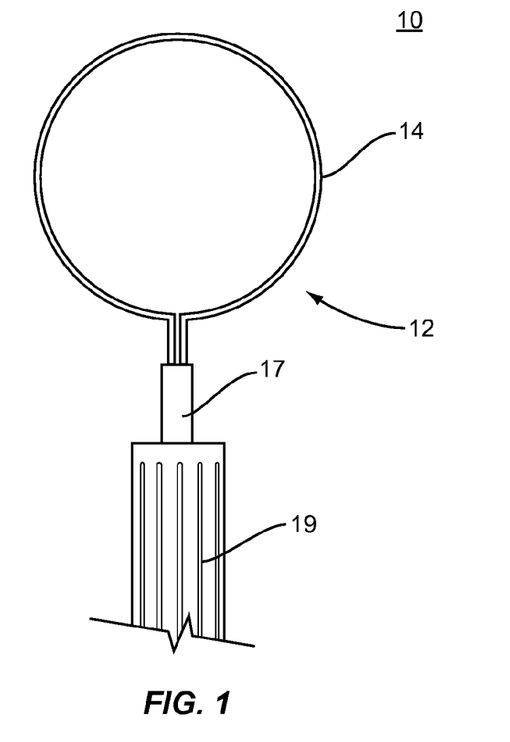
FIG. 1 is a partial top plan view of the device according to some embodiments of the present invention.

Referring now to the drawings, a plan view of a capsularhexis device according to some embodiments of the invention is illustrated in FIG. 1. Those skilled in the art will appreciate that FIG. 1, like the several other attached figures, is not to scale, and that several of the features may be exaggerated to more clearly illustrate the features of the invention. Those skilled in the art will also appreciate that the illustrated structures are only exemplary, and not limiting.

In any case, the capsularhexis device 10 of FIG. 1 includes a bare heating element 12 made of a fine, superelastic wire 14. In particular, the wire 14 may be formed from a nickel titanium alloy, commonly known as Nitinol, which exhibits superelastic and shape memory properties. Because it is superelastic (which term is intended herein as a synonym for the somewhat more technically precise term "pseudoelastic"), an object made from Nitinol can withstand a significant amount of deformation when a load is applied and return to its original shape when the load is removed. (Those skilled in the art will appreciate that this property is distinct from, although related to, "shape memory", which refers to a property exhibited by some materials in which an object that is deformed while below the material's transformation temperature returns to its former shape when warmed to above the transformation temperature. Nitinol exhibits both properties; superelasticity is exhibited above the transformation temperature.) Further, Nitinol is resistive, and can thus be heated with an electrical current, making it useful for forming the resistive-heating element 12 illustrated in FIG. 1. Of course, those skilled in the art will appreciate that other materials that are resistive and superelastic may be used instead of Nitinol in some embodiments of the invention.

The resistive-heating element 12 of FIG. 1 comprises a loop formed from the superelastic wire 14. The ends of the wire 14, extending away from the loop to form a lead section, are kept electrically separate with a flexible, electrically insulating material 17. In the pictured embodiment, the insulating material 17 completely surrounds a portion of the lead section. However, those skilled in the art will appreciate that insulating material 17 may surround only one lead, or may only partially surround either or both leads, in some embodiments, provided that the two leads extending away from the loop and into the handle 19 are kept electrically separate so that electrical current may be passed through the loop of the resistive-heating element 12. Insulating material 17 preferably comprises a bio-compatible and high temperature-resistant material, such as polyimide or Teflon.

Handle 19 in the pictured embodiment is a flat or cylindrical tube that rigidly engages a portion of the lead section, including the insulating material 17. Handle 19 may thus be used to insert the heating element 12 into the eye during the capsularhexis procedure and to retract the heating element 12 afterwards, as will be discussed in further detail below. The handle 19, which may be made from an inexpensive material such as a thermoplastic, may also contain electrical connectors and/or connecting wires so that the heating element 12 may be selectively connected to a power source for heating. In some embodiments, the handle 19, insulation material 17, and resistance-heating element 14 form a disposable unit that can be selectively connected during use to a handpiece or other apparatus that can supply electrical current.

Figure 2:
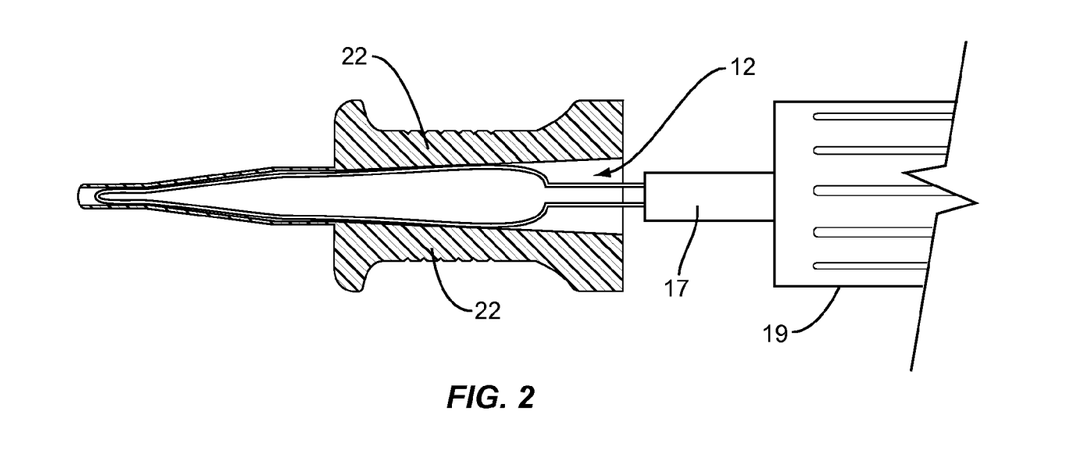
FIG. 2 illustrates a capsularhexis device according to some embodiments in which the resistive-heating element is retracted into a tubular insertion cartridge.

Because of its superelastic properties, the heating element 12 may be collapsed for insertion into the anterior chamber of the eye, regaining its pre-defined shape within the anterior chamber. Accordingly, some embodiments of the present invention include or may be used with an insertion tube through which the heating element 12 is pushed. An example is pictured in FIG. 2, which illustrates a collapsed heating element 12 in a retracted position within tubular insertion cartridge 22. The heating element 12 is collapsible upon retracting it into the insertion cartridge and expandable to its original shape upon ejection from the cartridge. In some embodiments, the interior portion of insertion cartridge 22 may be dimensioned to accommodate handle 19, so that the loop formed by heating element 12 may be fully ejected from the cartridge during use.

Figure 3A:
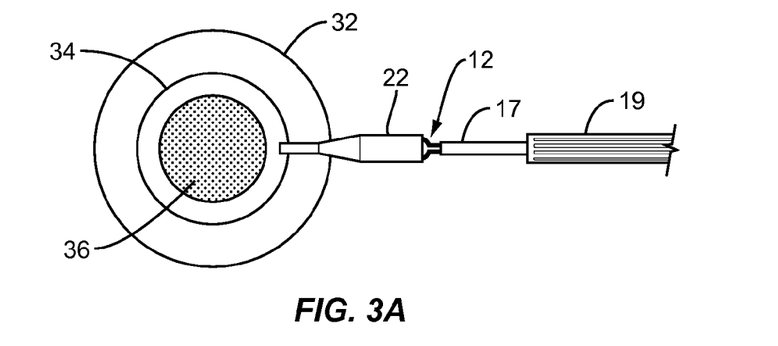
FIGS. 3A-3D illustrate the insertion and removal of a capsularhexis device during cataract surgery.

FIGS. 3A-3D illustrate the insertion of the heating element 12 into an eye 32, using an insertion cartridge 22. Prior to the procedure, the loop of the heating element 12 has been withdrawn into the insertion cartridge, so that in FIG. 3A, the loop of heating element 12 is contained almost entirely within the cartridge 22. Thus, the leading tip of the apparatus can be inserted into the anterior chamber 34 of the eye 32, as shown in FIG. 3A, through a small incision.

Figure 3B:
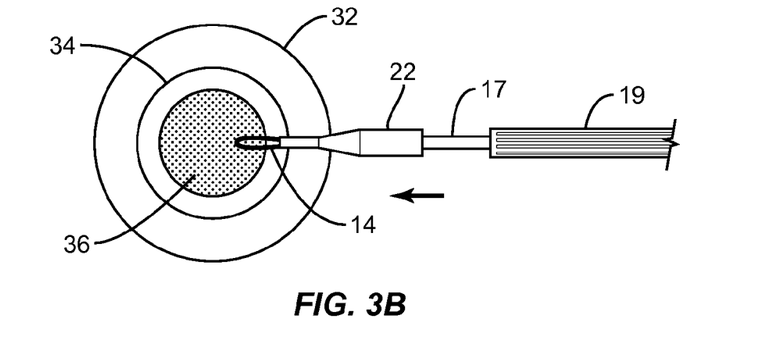
Figure 3C:
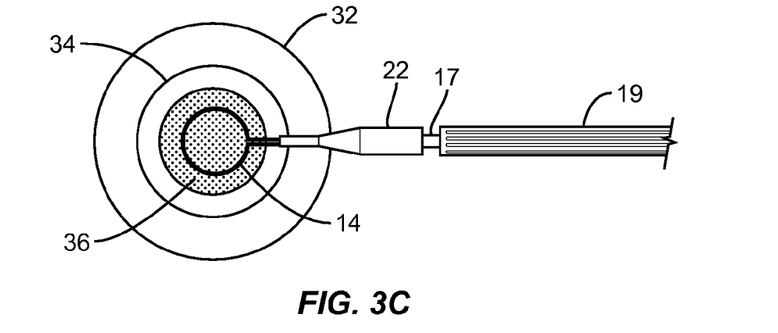
Figure 3D:
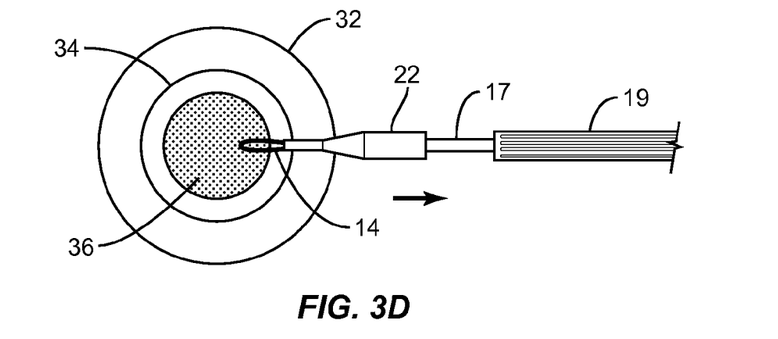

Using handle 19, the collapsed heating element 12 is pushed through the cartridge 22, as shown in FIG. 3B, until it is completely within the anterior chamber 34. The loop of the heating element 12 then regains its pre-determined shape, as shown in FIG. 3C, and is then positioned against the capsule 36. The heating element 12 is then energized, e.g., with a short pulse or series of pulses of current. As discussed above, this heating sears the capsule 36, effectively creating a smooth continuous cut on the capsule. The heating element 12 may then be retracted into the insertion cartridge 22, as shown in FIG. 3D, and then removed from the eye 32. The cut portion of the capsule may be readily removed using a conventional surgical instrument, such as forceps.

Figure 4:
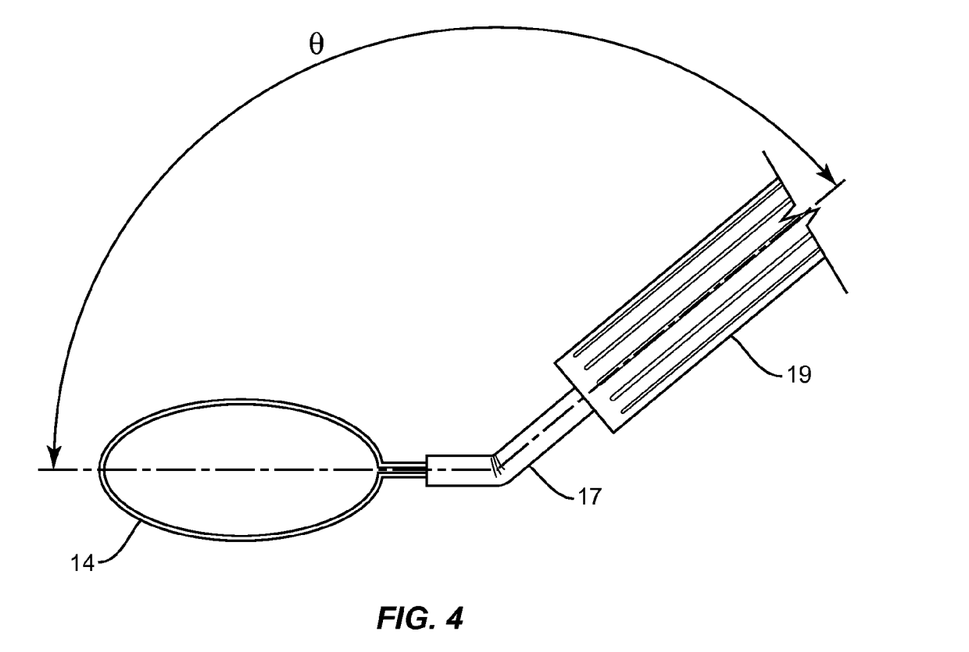
FIG. 4 illustrates the bending of a lead portion of an exemplary capsularhexis device to a pre-determined angle.

Because the superelastic wire 14 is flexible, as is the insulation material 17 in some embodiments, the handle 19 may be bent upwards when the heating element 12 is placed against the capsule 36. Because the deformation properties of the wire 14 (and, in some cases, the insulation 17) can be readily determined for a given device, the bending angle formed with respect to the plane of the heating element 12 may be used as an indication of the force applied to the capsule 36 by the heating element 12. Thus, a range of acceptable bending angles may be defined for a particular device, to correspond to a range of desirable application forces for optimal cauterization of the capsule 36. Accordingly, a surgeon may conveniently achieve a desired contact force between the heating element 12 and the capsule 36 by simply manipulating the bending angle to match or approximately match a pre-determined angle $\theta$, as shown in FIG. 4.

Figure 5A:
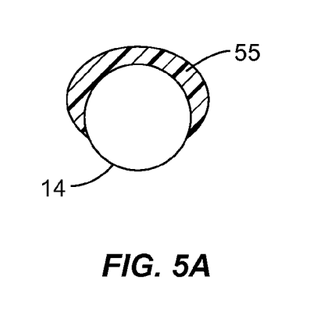
FIGS. 5A and 5B are cross-sectional views of exemplary resistive-heating elements according to some embodiments of the invention.
Figure 5B:
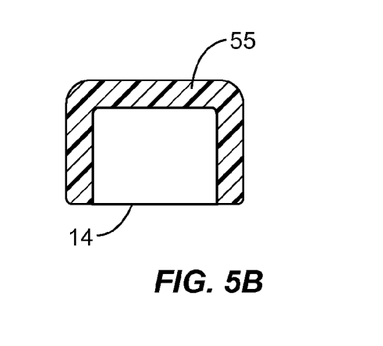

As was discussed above, some embodiments of the present invention include a bare wire made of Nitinol (or other superelastic material). To further reduce any potential collateral damage to tissue near the heating element, some embodiments of the present invention may include a thermally insulating layer disposed on at least a top face of the loop formed by the resistive-heating element 12, such that a bottom face, which is disposed against the capsule during the capsularhexis procedure, is left bare. A cross-sectional view of one such embodiment is pictured in FIG. 5A, which shows a cross-section of a round wire 14, partially surrounded with a thermally insulating layer 55. In some embodiments, the superelastic wire 14 may have a square or rectangular cross-section, as shown in FIG. 5B, in which case the thermally insulating material 55 may be conveniently disposed on three sides of the wire 14. In either case, the insulating material 55 may be disposed on the wire 14 around all or substantially all of the loop of the resistive-heating element 12.

Figure 6:
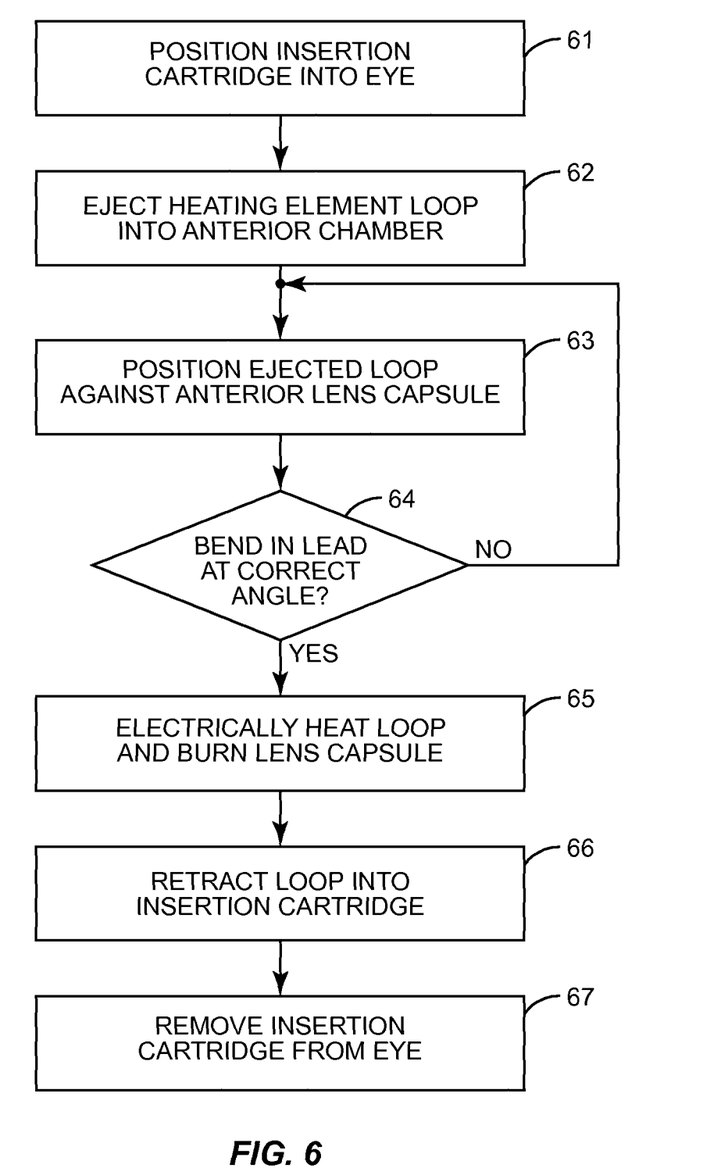
FIG. 6 is a process flow diagram illustrating an exemplary method for utilizing a capsularhexis device.

With the above-described device configurations in mind, those skilled in the art will appreciate that FIG. 6 illustrates a method for utilizing a capsularhexis device according to some embodiments of the present invention. The illustrated procedure begins with the positioning of an insertion cartridge into the eye, as illustrated at block 61, and the ejection of the heating element loop into the anterior chamber of the eye, as shown at block 62. Because the heating element 12 described herein may be collapsed, the insertion cartridge may be dimensioned to fit through an incision considerably smaller than the expanded diameter of the heating element's loop.

Once the loop of the heating element is ejected into the eye, it may be positioned against the anterior lens capsule, as shown at block 63. In some embodiments of the invention, the applied force between the heating element and the capsule may be gauged by assessing a bend in the lead section of the heating element. In other words, the angle between the handle and the plane formed by the heating element may be matched to a pre-determined angle, as shown at block 64, to ensure that the correct force is applied.

As shown at block 65, after the heating element is correctly positioned against the capsule it is energized by the application of electrical current, so that the loop is heated and "burns" the lens capsule. Once the burning of the capsule is complete, the heating element may be retracted into the insertion cartridge, as shown at block 66, and removed from the eye, as shown at block 67.

As was briefly discussed above, the energizing of the resistance-heating element may advantageously comprise a short pulse (e.g., 20 milliseconds) of electrical current, or a series of pulses (e.g., 1 millisecond each). Those skilled in the art will appreciate that the power settings (e.g., voltage, current, pulse width, number of pulses, etc.) should be established for a particular heating element configuration so that a continuous, circular (or oval) through-cut on the capsule can be attained, while minimizing collateral damage to portions of the capsule surrounding the portion to be removed. When determining the power settings for a particular heating element according to those described herein, those skilled in the art should consider that multiple working mechanisms may contribute to the "cutting" of the capsule. For instance, a steam "explosion" in the viscoelastic material caused by rapid heating of the heating element may contribute to the cut-through of the capsule, in addition to the thermal breakdown of the capsule material.

The preceding description of various embodiments of a capsularhexis device and methods for utilizing a capsularhexis device was given for purposes of illustration and example. Those skilled in the art will appreciate, of course, that the present invention may be carried out in other ways than those specifically set forth herein without departing from essential characteristics of the invention. The present embodiments are thus to be considered in all respects as illustrative and not restrictive, and all changes coming within the meaning and equivalency range of the appended claims are intended to be embraced therein.

What is claimed is:

1. A capsularhexis device, comprising:
   a tubular insertion cartridge;
   a resistive-heating element comprising an electrically resistive, superelastic wire having first and second ends, the superelastic wire formed to include a loop and so that the first and second ends are adjacent and extend away from the loop to form a lead section, wherein the loop collapses as the loop is retracted completely into the tubular insertion cartridge and wherein the loop returns to the loop's original shape as the loop is pushed out of the tubular insertion cartridge;
   an insulation portion comprising an electrically insulating material that wraps around each of the first and second ends to electrically separate the first and second ends of the superelastic wire such that current enters the loop through one of the first and second ends, flows continuously through the loop, and exits the loop through the other of the first and second ends; and
   a handle fixedly engaging at least a portion of the lead section;
   wherein at least a bottom surface of the loop from the first end, of the lead section, around the loop to the second end, of the lead section, is bare such that the loop forms a continuous loop-shaped burn on a lens capsule during application of current for a capsularhexis.

2. The capsularhexis device of claim 1, wherein the tubular insertion cartridge is configured to fit around the handle portion.

3. The capsularhexis device of claim 1, wherein the superelastic wire is formed from a nickel titanium alloy.

4. The capsularhexis device of claim 1,
   wherein the bottom surface of the loop is configured for placing against the anterior lens capsule of an eye,
   wherein the loop further comprises a top surface, opposite the bottom surface, and
   wherein the resistive-heating element further comprises a thermally insulating layer disposed on at least the top surface but absent from the bottom surface.

5. The capsularhexis device of claim 1, wherein the superelastic wire has a rectangular cross section around at least substantially the entire loop, and wherein the thermally insulating layer is disposed on three sides of the superelastic wire around at least substantially the entire loop.

6. The capsularhexis device of claim 1, wherein the resistive-heating element and insulation portion are configured to form a circular cut in a lens capsule.

7. The capsularhexis device of claim 1, wherein at least one of the first or second ends is surrounded by the insulation portion.

8. The capsulorhexis device of claim 1, wherein the loop, while collapsed inside the tubular insertion cartridge, can pass through approximately a 2 millimeter incision in the cornea.

9. The capsulorhexis device of claim 1, wherein the entire loop from the first end, of the lead section, around the loop to the second end, of the lead section, is bare such that the loop forms a continuous loop-shaped burn on a lens capsule during application of current for a capsularhexis.

10. The capsularhexis device of claim 1, wherein the first and the second ends remain adjacent both when the loop is in a collapsed configuration inside the tubular insertion cartridge and when the loop is pushed out of the tubular insertion cartridge.

* * * * *